United States Patent [19]

Ikeda et al.

[11] Patent Number: 5,892,061
[45] Date of Patent: Apr. 6, 1999

[54] PROCESS FOR PREPARING ISOIMIDES

[75] Inventors: Kan Ikeda; Wataru Yamashita; Shoji Tamai, all of Fukuoka-ken, Japan

[73] Assignee: Mitsui Chemicals, Inc., Tokyo, Japan

[21] Appl. No.: 975,506

[22] Filed: Nov. 21, 1997

[51] Int. Cl.⁶ .................... C07D 307/66; C07D 307/88; C08G 69/26
[52] U.S. Cl. .................. 549/303; 525/436; 528/353; 549/320; 549/321; 549/299; 560/110; 560/250; 560/253
[58] Field of Search ..................... 549/303, 320, 549/321, 299; 560/110, 250, 253; 528/353; 525/436

[56] References Cited

U.S. PATENT DOCUMENTS

| | | | |
|---|---|---|---|
| 2,937,187 | 5/1960 | Wheeler et al. | 549/303 |
| 2,998,429 | 8/1961 | Sauers et al. | 549/321 |
| 3,035,065 | 5/1962 | Sauers et al. | 549/321 |
| 4,179,444 | 12/1979 | Roth | 549/321 |
| 4,784,707 | 11/1988 | Wefers et al. | 156/48 |
| 5,254,412 | 10/1993 | Fujimoto | 428/473.5 |

*Primary Examiner*—Bernard Dentz
*Attorney, Agent, or Firm*—Burns, Doane, Swecker Mathis, L.L.P.

[57] ABSTRACT

A preparation process of isoimide comprising reacting a compound having one or more carboxyl group and one or more amide bond in the same molecule in the presence of a haloiminium salt and basic substance, and a preparation process of isoimide comprising reacting a compound having one or more carboxyl group with a compound having one or more amide bond in the presence of a haloiminium salt and basic substance are disclosed.

21 Claims, 5 Drawing Sheets

PROCESS FOR PREPARING ISOIMIDES

BACKGROUND OF THE INVENTION

1. Field of the Invention

The present invention relates to a novel preparation process of isoimide comprising reacting in the presence of a haloiminium salt and basic substance.

2. Related Art of the Invention

Phenylmaleisoimide, N,N-phenylenebisisomaleimide, phenylisophthalimide and other isoimide monomers are useful compounds which are known as a raw material monomers and intermediate of agricultural chemicals and medicines. Preparation process of these isoimide has been conventionally known. For example, U.S. Pat. No. 2,998,429 has disclosed a process for ring-closing maleamic acid and converting to a corresponding isoimide isomer by using triethylamine in the presence of dichloroacetyl chloride. U.S. Pat. No. 3,035,065 has described a process for converting to a corresponding isoimide isomer in the presence of dicyclohexylcarbodiimide. However, these processes have a problem of high cost.

Further, as an improvement of these processes, Japanese Laid-Open Patent SHO 52-97959 has disclosed a preparation process of corresponding isoimide by reacting amic acid with ketene in the presence of acetic anhydride. However, at least an equimolar amount of expensive ketene for amic acid is required in order to form a proper amount of isoimide. Ketene is a very labile compound and thus the above process using ketene is also unfavorable as a preparation process in industry.

It has also been known as a preparation process of isoimide to react amic acid or polyamic acid with acetic anhydride, ethyl chloroformate and triethylamine, trifluoroacetic anhydride and other dehydrating agents. However, any of these processes involve many problems, for example, the reaction has slow velocity and low selectivity, excessive facilities are required for separation and recovery of byproducts, and it is difficult to repeatedly use the recovered substances.

On the other hand, polyisoimide which is known as a polyimide precursor can isomerize with ease to polyimide by heat treatment without evolution of water or other low molecular weight compounds, and is thus a material of being focused attention as a polyimide precursor in place of polyamic acid.

Japanese Laid-Open Patent HEI 4-214728 has disclosed a preparation process of polyisoimide which uses a nontoxic dihydroquinoline derivative as a dehydrating agent and does not require separation of solid byproducts. The process is specifically characterized in the nontoxic dehydrating agent. However, the process also forms four species of byproduct and a quinoline byproduct requires a great labor in order to regenerate the dihydroquinoline derivative. These problems have inhibited reduction in the production cost.

SUMMARY OF THE INVENTION

The object of the invention is to provide a novel process which can simply prepare isoimide.

As a result of an intensive investigation in order to overcome the above problems, the present inventors have found that isoimide is surprisingly formed in high selectivity within a short time by reaction of a compound having a carboxyl group and amide bond in the same molecule in the presence of a haloiminium salt and basic substance or by reaction of a compound having a carboxyl group with a compound having an amide bond in the presence of a haloiminium salt and basic substance. Thus the invention has been completed.

That is, the aspect of the invention is (A) a preparation process of isoimide comprising reacting a compound having one or more carboxyl group and one or more amide bond in the same molecule in the presence of a haloiminium salt and basic substance.

Another aspect of the invention is (B) a preparation process of isoimide comprising reacting a compound having one or more carboxyl group with a compound having one or more amide bond in the presence of a haloiminium salt and basic substance.

In the former preparation process (A), the compound having one or more carboxyl group and one or more amide bond is represented by one of the formula (1), (2) or (3) below or a mixture of the same:

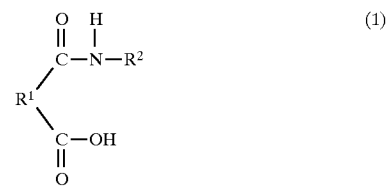

wherein $R^1$ is an unsubstituted or substituted divalent hydrocarbon group, individually selected from an aliphatic group and aromatic group, have a saturated bond and/or unsaturated bond, and $R^2$ is an unsubstituted or substituted monovalent hydrocarbon group, individually selected from an aliphatic group and aromatic group, have a saturated bond and/or unsaturated bond,

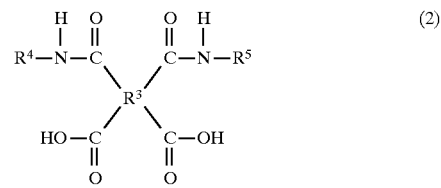

wherein $R^3$ is an unsubstituted or substituted tetravalent hydrocarbon group, is an aliphatic group or aromatic group, and has a saturated bond and/or unsaturated bond; $R^4$ and $R^5$ are an unsubstituted or substituted monovalent hydrocarbon group, individually selected from an aliphatic group and aromatic group, have a saturated bond and/or unsaturated bond, and are the same or different,

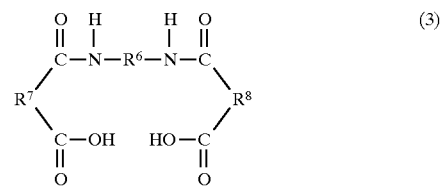

wherein $R^6$ is an unsubstituted or substituted divalent hydrocarbon group, is an aliphatic group or aromatic group, and has a saturated bond and/or unsaturated bond; $R^7$ and $R^8$ are an unsubstituted or substituted divalent hydrocarbon group and are the same or different.

Further, in the preparation process (A), the compound having one or more carboxyl group and one or more amide bond in the same molecule is a homopolymer or copolymer having recurring units represented by the formula (4) and/or formula (5) below.

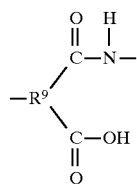

(4)

wherein $R^9$ is an unsubstituted or substituted trivalent hydrocarbon group, is an aliphatic group or aromatic group, and has a saturated bond and/or unsaturated bond.

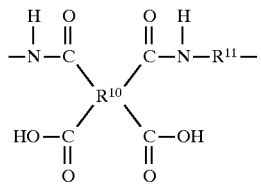

(5)

wherein $R^{10}$ is an unsubstituted or substituted tetravalent hydrocarbon group, is an aliphatic or aromatic group, and has a saturated bond and/or unsaturated bond; $R^{11}$ is an unsubstituted or substituted divalent hydrocarbon group, is an aliphatic group or aromatic group, and has a saturated bond and/or unsaturated bond.

Further, in these preparation processes, the compound having one or more carboxyl group and one or more amide bond in the same molecule is selected from:

① a compound obtained by reacting a compound having one or more amino group with a compound having one or more carboxyl group, ② a compound obtained by reacting a compound having one or more amino group with a compound having one or more acid halogenide group and one or more carboxyl group in the same molecule, ③ a compound obtained by reacting a compound having one or more amino group with a compound having two or more acid halogenide group in the same molecule and successively converting the unreacted acid halogenide group in the resulting molecule to a carboxyl group, ④ a compound obtained by reacting a compound having one or more amino group with a compound having two or more carboxyl group, ⑤ a compound obtained by reacting a compound having one or more amide bond with a compound having one or more carboxyl group or ⑥ a polymer of amino acid.

Moreover, in the latter preparation process (B), the compound having one or more amide bond is represented by one of the formula (6), (7) or (8) below or a mixture of the same.

(6)

wherein $R^{12}$ and $R^{13}$ are an unsubstituted or substituted monovalent hydrocarbon group, individually selected from an aliphatic group and aromatic group, have a saturated bond and/or unsaturated bond, and are the same or different,

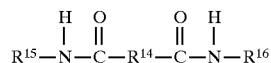

(7)

wherein $R^{14}$ is an unsubstituted or substituted divalent hydrocarbon group, is an aliphatic group or aromatic group, and has a saturated bond and/or unsaturated bond; $R^{15}$ and $R^{16}$ are an unsubstituted or substituted monovalent hydrocarbon group, individually selected from an aliphatic group and aromatic group, have a saturated bond and/or unsaturated bond, and are the same or different,

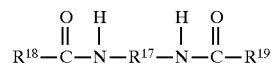

(8)

wherein $R^{17}$ is an unsubstituted or substituted divalent hydrocarbon group, is an aliphatic group or aromatic group, and has a saturated bond and/or unsaturated bond; $R^{18}$ and $R^{19}$ are an unsubstituted or substituted monovalent hydrocarbon group, individually selected from an aliphatic group and aromatic group, have a saturated bond and/or unsaturated bond, and are the same or different.

In the preparation process (B), the compound having one or more amide group is a homopolymer or copolymer having recurring units represented by the formula (9) and/or formula (10) below.

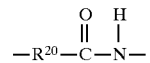

(9)

wherein $R^{20}$ is an unsubstituted or substituted divalent hydrocarbon group, is an aliphatic group or aromatic group, and has a saturated bond and/or unsaturated bond,

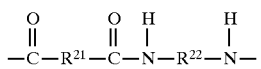

(10)

wherein $R^{21}$ and $R^{22}$ are unsubstituted or substituted divalent hydrocarbon group, individually selected from an aliphatic group and aromatic group, have a saturated bond and/or unsaturated bond, and are the same or different.

Further in these preparation processes, the compound having one or more amide bond is selected from:

⑦ a compound obtained by reacting a compound having one or more amino group with acid anhydride, ⑧ a compound obtained by reacting a compound having one or more amino group with a compound having one or more acid halogenide group, and ⑨ a compound obtained by reacting a compound having one or more amino group with a compound having one or more carboxyl group.

Moreover, in the above preparation processes (A) and (B), reaction temperature is from $-10°$ C. to $150°$ C.

The present invention has revealed that isoimide can be simply obtained at high selectivity within a short time by conducting the reaction in the coexistence of a haloiminium salt and basic substance.

DETAILED DESCRIPTION OF THE INVENTION

Figure 1:
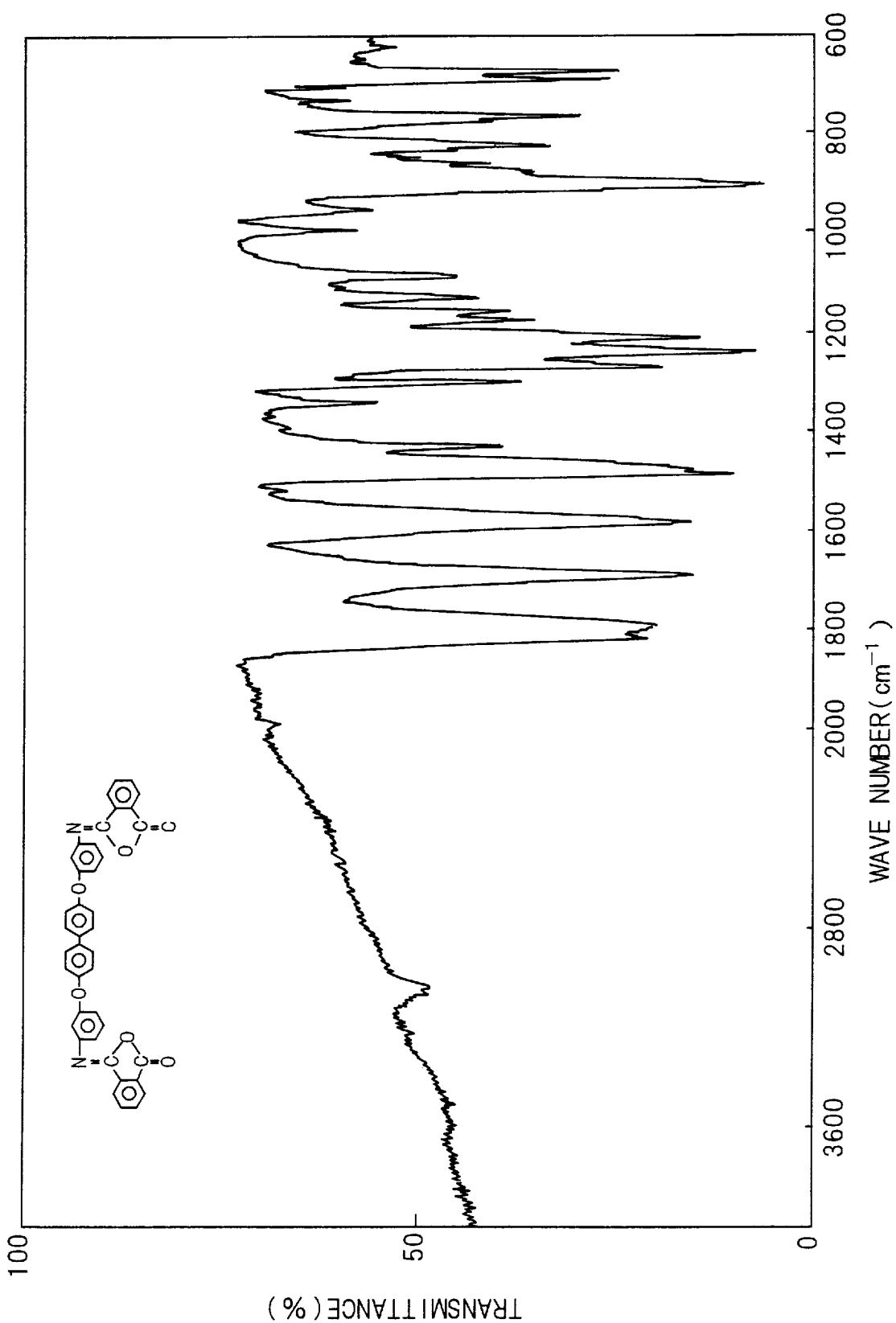
FIG. 1 shows an IR chart of 4,4'-bis(3-phthalisoimidophenoxy) biphenyl obtained in Example 9.

The present invention will hereinafter be illustrated in detail.

The haloiminium salt used in the invention is a compound comprising, in the molecule, a structure represented by the formula (11) below.

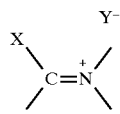 (11)

within X and Y are a halogen atom, and are the same or different.

Whether the salt is a cyclic compound or not leads to no problem as long as the salt comprises the above structure.

Representative haloiminium salts which can be generally used include, for example, N,N-dimethylchloromethyleneiminium chloride, N,N-diphenylcyclohexylmethyleneiminium chloride, N,N-diphenylchloro-p-methoxyphenylmethyleneiminium chloride, N,N,N',N'-tetramethylchloroform amidinium chloride, 2-chloro-1,3-dimethylimidazolinium chloride, 2-chloro-1,3-diethylimidazolinium chloride, 2-chloro-1,3-dipropylimidazolinium chloride, 2-chloro-1,3-dibutylimidazolinium chloride, 2-chloro-1,3-dihexylimidazolinium chloride, 2-chloro-1,3-dicyclohexylimidazolinium chloride, 2-chloro-1,3-diphenylimidazolinium chloride, 2-chloro-1,3-dimethyl-3,4,5,6-tetrahydropyrimidinium chloride and other chlorides. Fluorides, bromides and iodides can also be used similarly. These haloiminium salts can also be used in the form of powder, or applied without any problem by dissolving or suspending in a suitable solvent. These haloiminium salts can be used as a mixture.

When isoimidizing the whole pair of the carboxyl group and amide bond in the system, the amount of the haloiminium salt used in the invention is usually 0.8 to 6 times by weight, preferably 1 to 3 times by weight, more preferably 1 to 1.5 times by weight for the carboxyl group. When the amount is less than 0.8 time, isoimidation sometimes cannot be completed. On the other hand, use of more than 6 times is uneconomical. However, for example, in the case of partly isoimidizing the carboxyl group and amide bond of the compound, the amount of the haloiminium salt can be suitably changed depending upon the object.

The basic substance is used in the invention in order to efficiently remove hydrogen halogenide formed in the reaction system.

The term "basic substance" in the invention is a generic name of the compound which can deactivate hydrogen halogenide in the isoimide forming reaction by reacting with hydrogen halogenide to form salt or adduct or by decomposing hydrogen halogenide.

Specific basic substances which can be used include, for example, trimethylamine, triethylamine, N,N-dimethylcyclohexylamine and other aliphatic tertiary amines; N,N-dimethylaniline, N,N-diethylaniline, N,N-dimethylbenzylamine, N,N-diethylbenzylamine and other aromatic tertiary amines; pyridine, piperidinopyridine, pyridinemethanol, piperazine, (hydroxyethyl)piperazine, N,N-dimethylpiperazine, N,N-diethylpiperazine, N-ethylpiperidine, N-methylpiperadine, 4-methylmorpholine, 4-ethylmorpholine, 1,8-diazabicycloundecene, α-picoline, β-picoline, γ-picoline, 2-pipecoline, 3-pipecoline, 4-pipecoline, 2-(1-piperazinyl) pyrimidine, pyrazine, pyrrolidine, o-phenanthroline and other heterocyclic tertiaryamines; and sodium hydroxide, potassium hydroxide and other inorganic alkali salts. However, no particular restriction is imposed upon these basic substances as long as the object for use can be attained.

These basic substances are used in a stoichiometric amount or more for hydrogen halogenide formed by the reaction of haloiminium salt and carboxyl group. The amount is usually 1 to 10 times, preferably 1 to 5 times, more preferably 1 to 2 times the stoichiometric amount. Use of less than stoichiometric amount leads to slow reaction velocity or reduction of yield. Use of more than 10 times is not needed and uneconomical.

The term "isoimide" in the invention is a generic name of the compound comprising the structure shown by the formula (12) below.

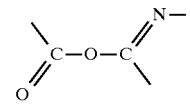 (12)

No particular restriction is imposed upon whether the compound is cyclic or not, other substituents which are comprised in the molecule, and molecular weight of the compound.

The raw materials used in the invention are briefly divided into two species. One species is (A) a compound having one or more carboxyl group and one or more amide bond in the same molecule. The other species is (B) a combination of a compound having one or more carboxyl group and a compound having one or more amide group. In both cases, the reaction product is a compound comprising the isoimide bond shown by the formula (12) above.

The compound having one or more carboxyl group and one or more amide bond in the same molecule includes a compound having the structure represented by the formulas (1) to (3), a mixture of the same, and a polymer or copolymer having a structure of the formula (4) and/or formula (5).

These compounds are generally called amic acid or polyamic acid in the case of a polymer, and the carboxyl group and amide bond are located on the adjacent carbon atoms in these compounds. However, no particular restriction is put upon the compounds which do not fall under amic acid or polyamic acid as long as the compounds can form by the reaction an isoimide bond of the formula (12).

Further, the combination of a compound having one or more carboxyl group with a compound having one or more amide bond is generally a combination of carboxylic acid with an amide compound or polyamide. The compounds which can be used for the combination include a compound having the structure represented by the formulas (6) to (8), a mixture of the same, and a homopolymer or copolymer having recurring units represented by the formula (9) and/or formula (10). However, no particular limitation is imposed upon these compounds as long as an isoimide bond can be formed by the reaction.

Specific structure of monovalent hydrocarbon groups $R^2$, $R^4$, $R^5$, $R^{12}$, $R^{13}$, $R^{15}$, $R^{16}$, $R^{18}$ and $R^{19}$ in the formulas (1), (2), (6), (7) and (8) includes, for example, a methyl, ethyl, n-propyl, isopropyl, n-butyl, 1-methylpropyl, 2-methylpropyl, isobutyl, amyl, hexyl and cyclohexyl group and other structure shown by the following formula.

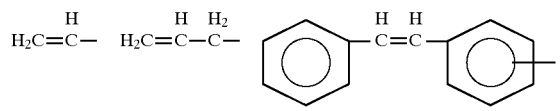

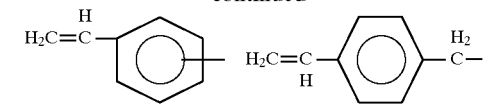
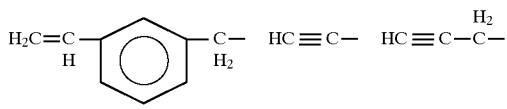
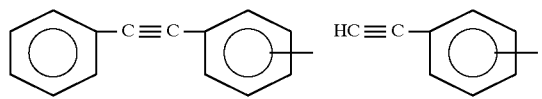
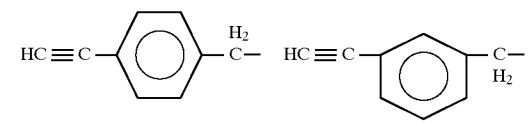
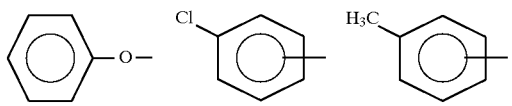
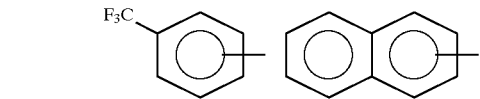
The divalent hydrocarbon group shown by $R^1$, $R^4$, $R^{11}$, $R^{14}$, $R^{17}$, $R^{20}$, $R^{21}$, $R^{22}$ in the formulas (1), (3), (5), (7), (8), (9) and (10) includes, for example, a methylene, ethylene, propylene, butylene and hexamethylene and other structure shown by the following formulas.
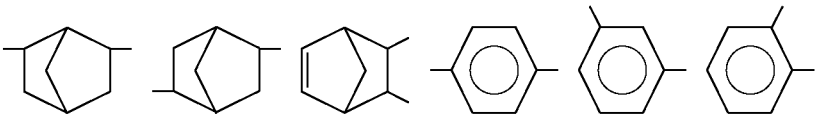
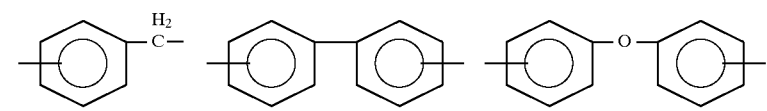
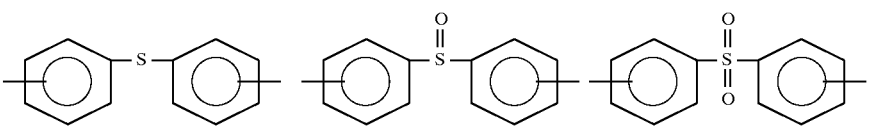
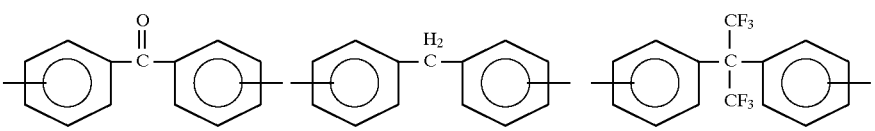

-continued
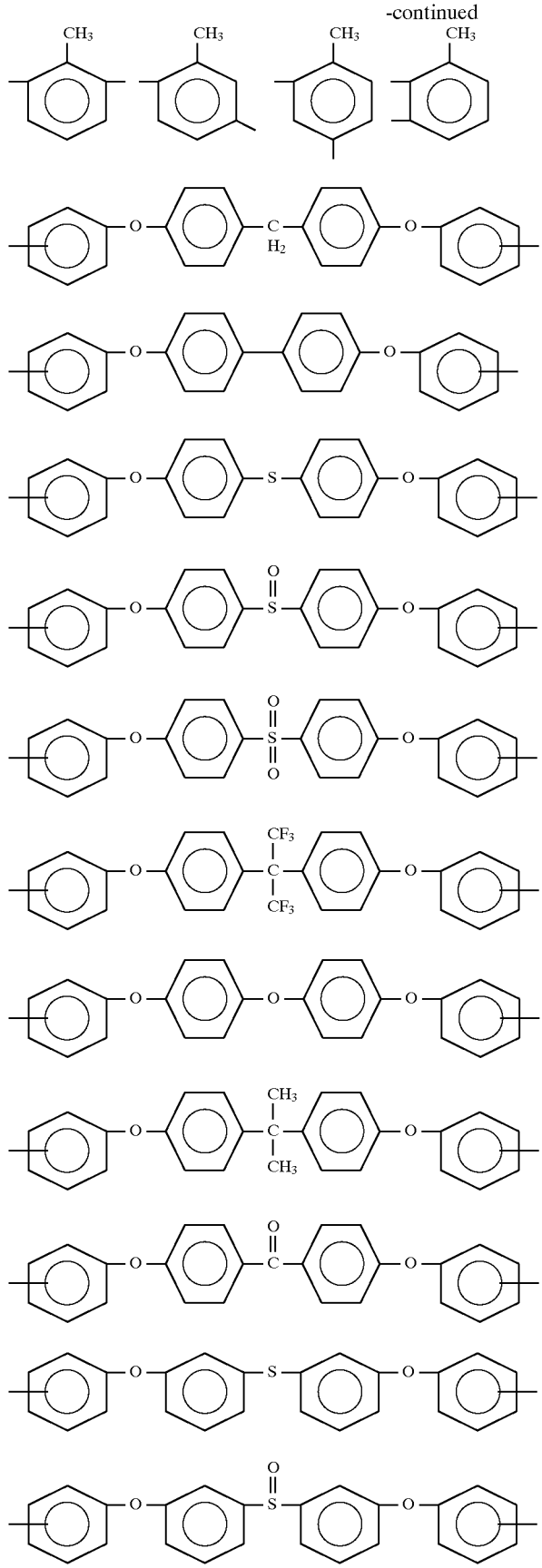

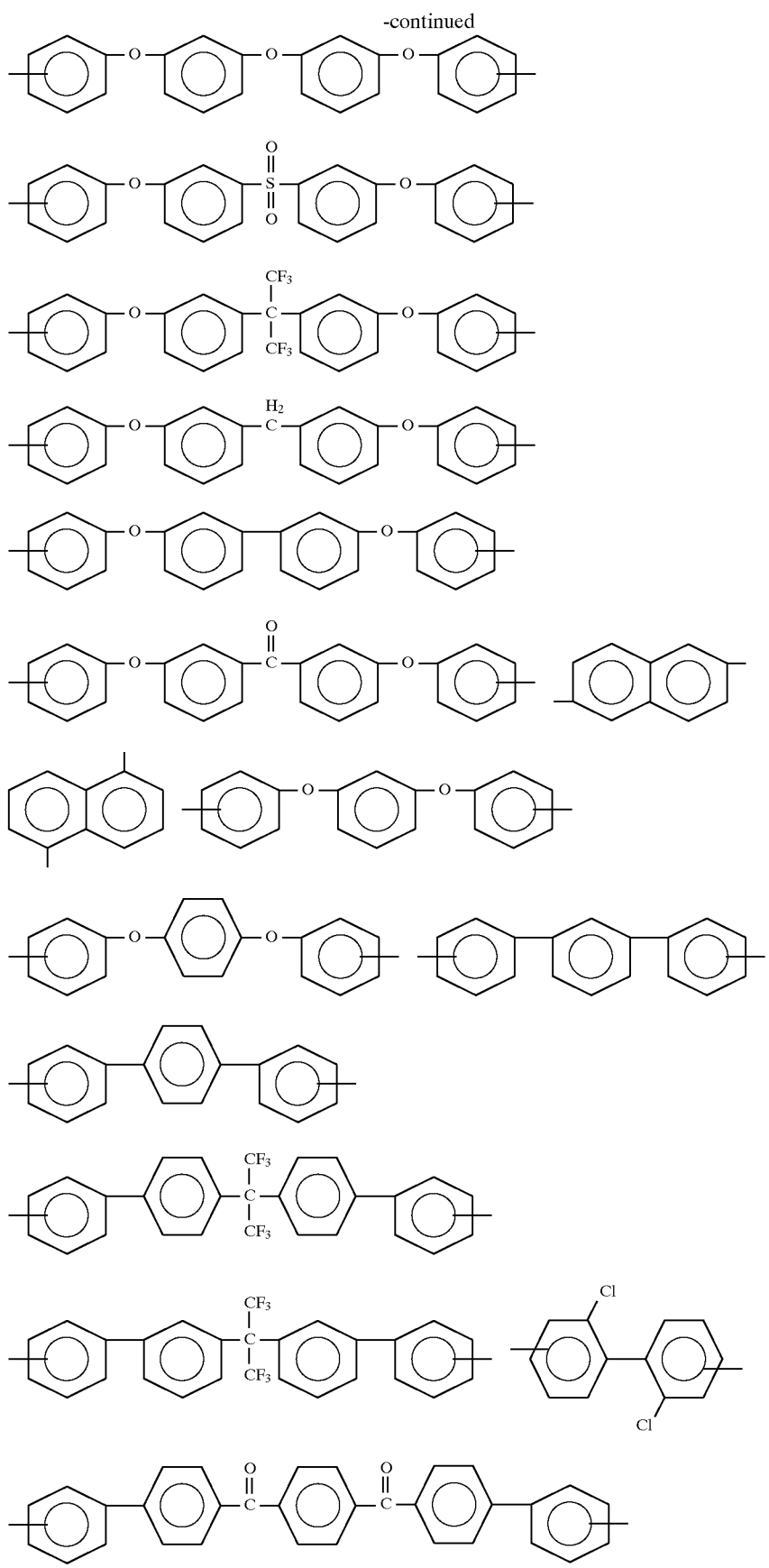

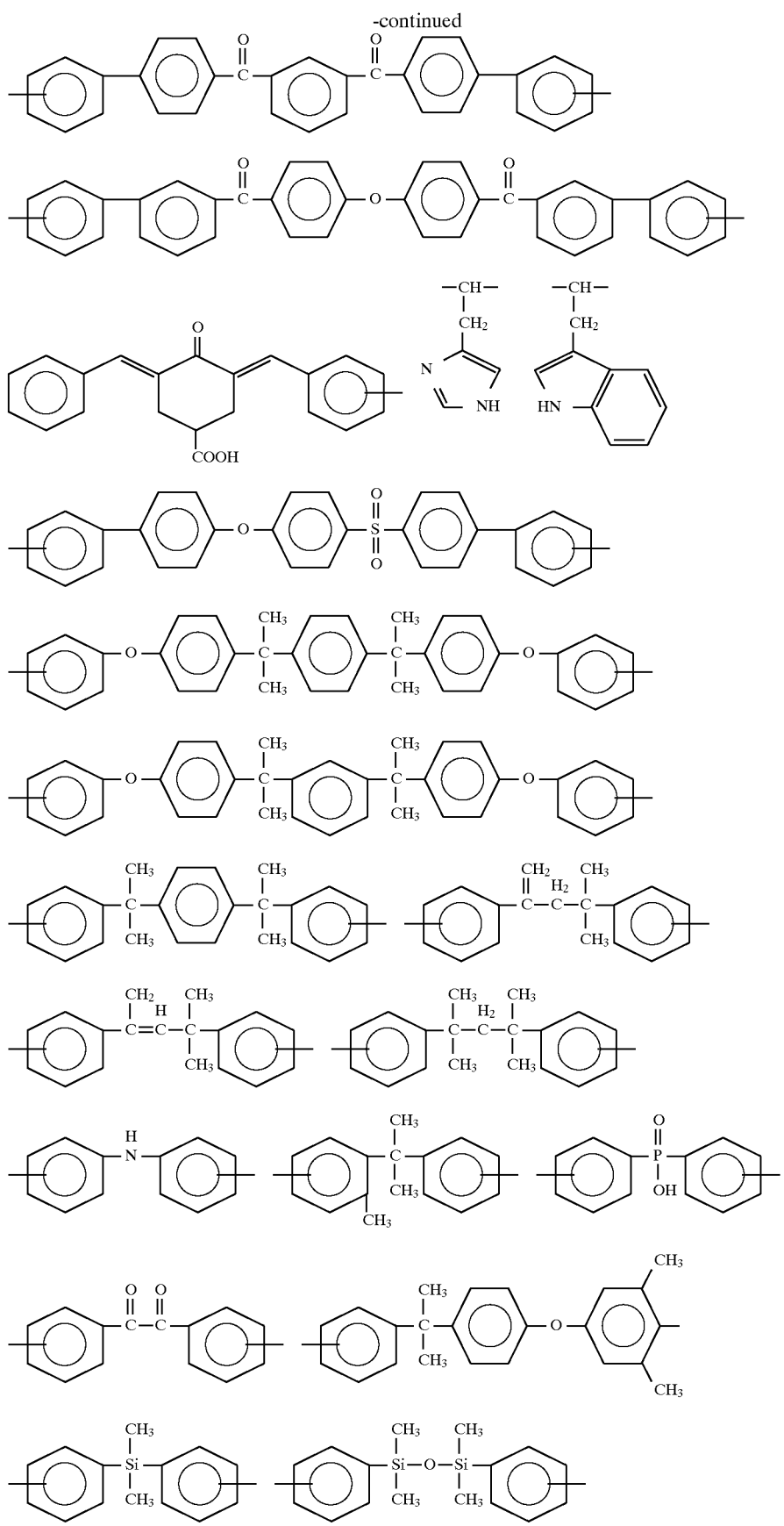

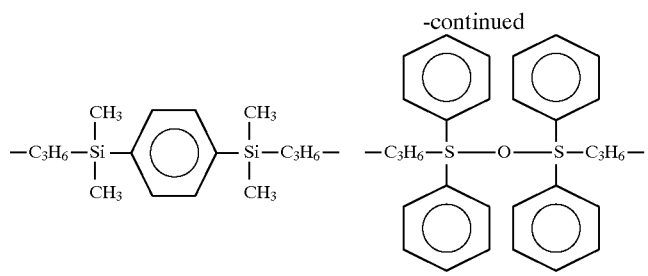
The trivalent hydrocarbon group shown by $R^9$ in the formula (4) includes the structure shown by the following formulas.
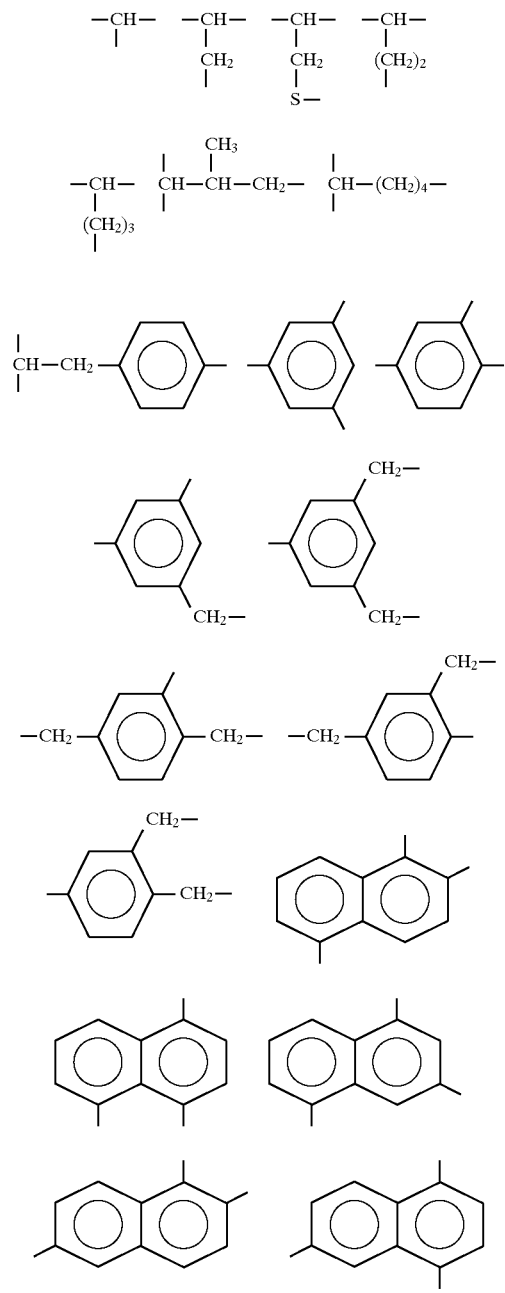
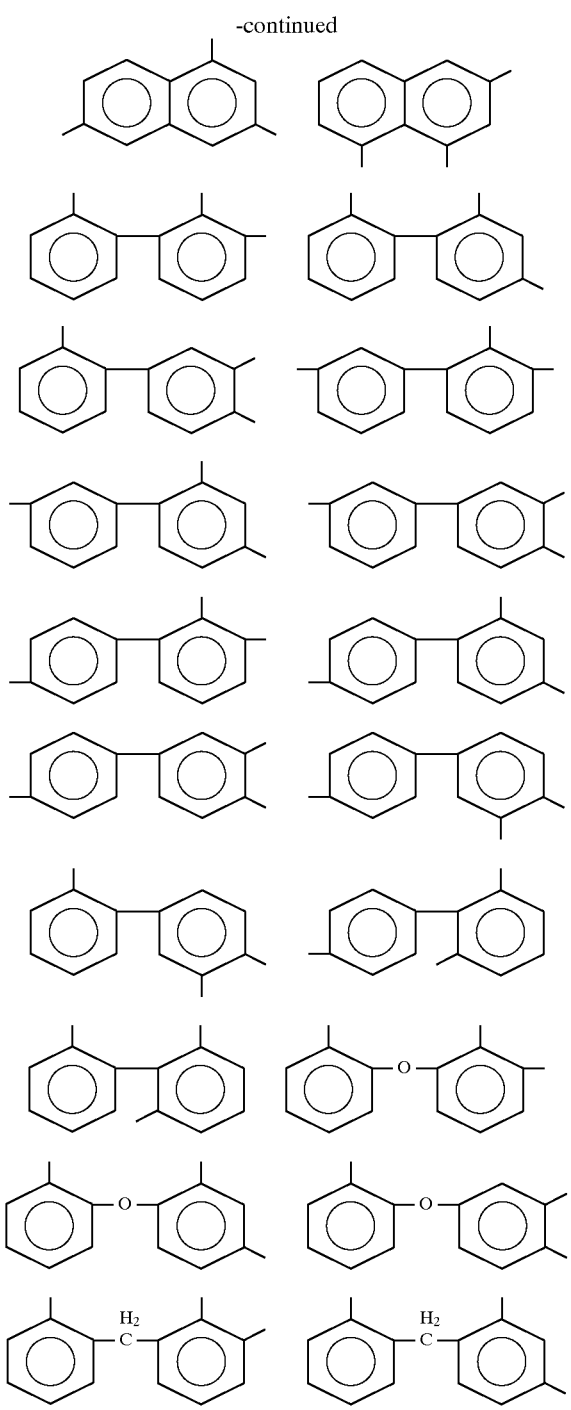

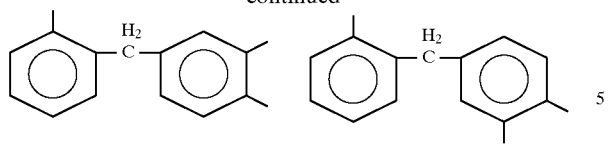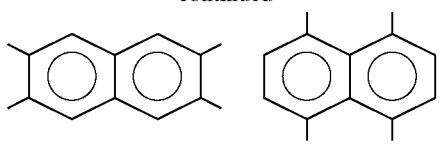
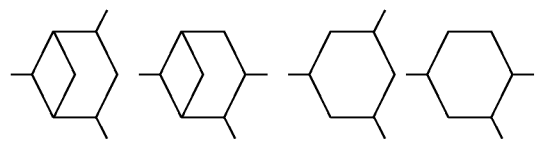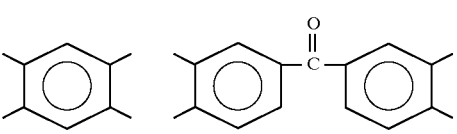
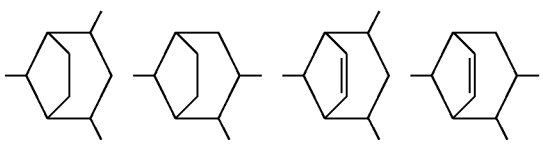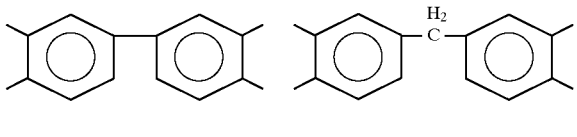
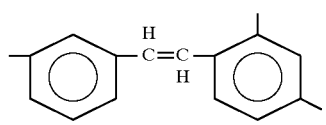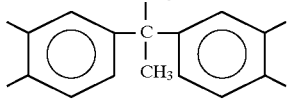
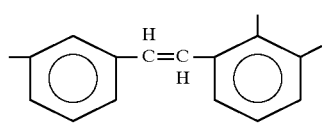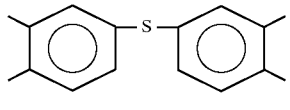
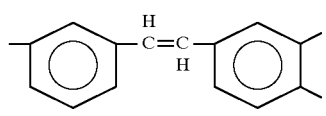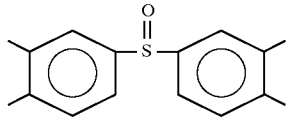
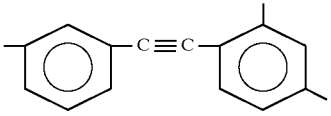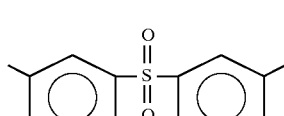
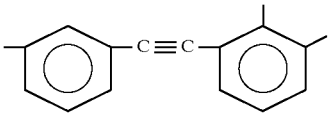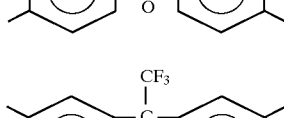
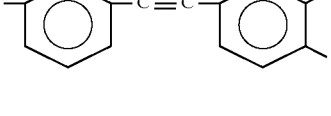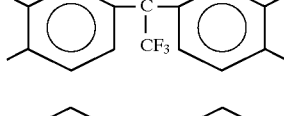
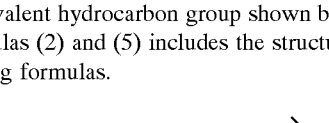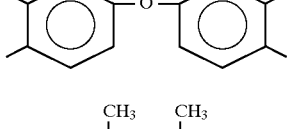
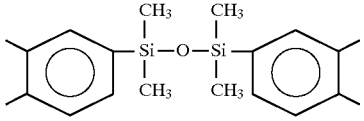
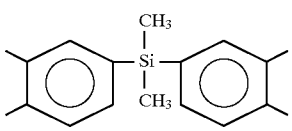
The tetravalent hydrocarbon group shown by $R^3$ and $R^{10}$ in the formulas (2) and (5) includes the structure shown by the following formulas.
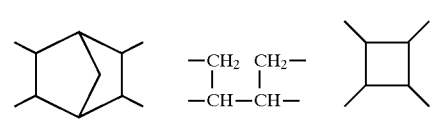
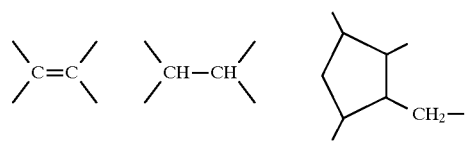
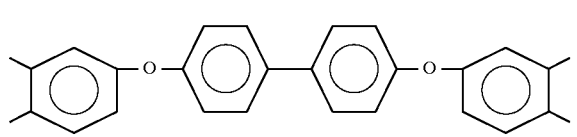

-continued

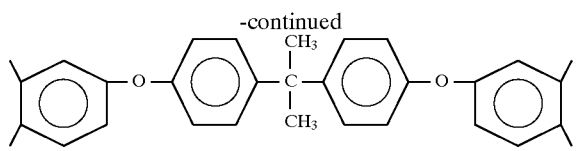

The compound having one or more carboxyl group and one or more amide bond in the same molecule can be generally obtained by ① reacting acid anhydride and/or acid dianhydride with a mono- or poly-valent amino compound. The compound can also be derived from ② a compound obtained by reacting a compound having an amino group with a compound having a carboxyl group and carboxylic acid halogenide group, ③ a compound obtained by reacting a compound having an amino group with a compound having two or more carboxylic acid halogenide group and successively converting the residual acid halogenide group to a carboxyl group, ④ a compound obtained by reacting a compound having an amino group with a compound having two or more carboxyl group, ⑤ a compound obtained by reacting a compound having an amide bond with a compound having a carboxyl group, or ⑥ a polymer of amino acid. No particular restriction is imposed upon the process for obtaining the compound as long as the compound has one or more carboxyl group and one or more amide bond.

Further, the compound having one or more amide bond can be derived from ⑦ a compound obtained by reacting a compound having an amino group with acid anhydride, ⑧ a compound obtained by reacting a compound having an amino group with a compound having a carboxylic acid halogenide group, and ⑨ a compound obtained by reacting a compound having an amino group with a compound having a carboxyl group. No particular restriction is put upon the process for obtaining the compound as long as the compound has one or more amide bond.

Representative compounds having one or more carboxyl group which can be used in the invention for reacting with a compound having one or more amide bond include, for example, formic, acetic, propionic, butyric, heptanic, isoacetic, crotonic, isocrotonic, trichloroacetic, trifluoroacetic, pyruvic, acrylic, benzoic, diphenyl-4-carboxylic, diphenylacetic, naphthoic, methylbenzoic, ethylbenzoic, nitrobenzoic, phenylacetic, bnzoylbenzoic, naphtholenecarboxylic acid and other monocarboxylic acid; and succinic, oxolic, malonic, glutaric, adipic, pimelic, suberic, azeloic, sebacic, undecane di-, dodecane di-, phenylsuccinic, itaconic, brasylic, 1,4-phenylenediacetic, maleic, fumaric, citraconic, naphthalenedicarboxylic acid and other polycarboxylic acid. No particular restriction is imposed upon these carboxyl compounds as long as these compounds can form an isoimide bond by reacting with an amide bond.

The reaction temperature in the invention differs depending upon the structure of isoimide and the molecular weight of polyisoimide, and is usually in the range of −10 to 150° C., preferably −10 to 100° C., more preferably −10 to 80° C., most preferably 0 to 60° C. The reaction temperature exceeding 150° C. leads to isomerzation of an isoimide bond to an imide bond. On the other hand, the reaction temperature lower than −10° C. requires excess labor for cooling and causes insufficient isoimidization.

Solvents can be used for carrying out the reaction in the invention.

Exemplary solvents which can be used include, for example, hexane, cyclohexane, heptane, benzene, toluene, xylene, mesitylene and other hydrocarbon solvents; carbon tetrachloride, methylene chloride, chloroform, 1,2-dichoroethane, chlorobenzene, dichlorobenzene, flourobenzene and other halogenated hydrocarbon solvents; diethyl ether, tetrahydrofuran, 1,4-dioxane, methoxybenzene and other ethers solvents; acetone, methyl ethyl ketone and other ketone slovents; and N,N-dimethylformamide, N,N-dimethylacetamide, N-methyl-2-pyrrolidone, 1,3-dimethyl-2-imidazolidinone, dimethylsulfoxide, sulfolane and other aprotic polar solvents. However, no particular restriction is imposed upon these solvents.

When isoimide powder is desired, the isoimide powder can be obtained with ease by conducting the reaction in an insoluble solvent of isoimide and filtering after termination of the reaction. When the reaction is carried out in a solvent which can dissolve isoimide. An isoimide solution is obtained as intact after finishing the reaction. Further, a polyisoimide solution can also be prepared by dissolving polyisoimide powder in a solvent capable of dissolving polyisoimide.

The process of the invention has higher selectivity and velocity of the reaction as compared with a conventionally known isoimidizing agent such as dicyclohexylcarbodiimide and trifluoroacetic anhydride. Consequently, isoimide can be obtained at high yield within a short time by the process of the invention as compared with conventionally known processes.

Conventionally known preparation processes had problems upon recovery and regeneration of the isoimidizing agent.

On the other hand, the process of the invention can carry out the recovery and regeneration with ease. In the process of the invention, a compound having an oxygen atom in place of the halogen atom of a haloiminium salt (hereinafter referred to as haloiminium salt raw material) can be readily recovered as a byproduct of the reaction by way of distillation and other known methods from the liquid which was separated from isoimide after finishing the reaction. Further, as disclosed in Japanese Laid-Open Patent SHO 59-25375, the haloiminium salt can be regenerated with easy by known processes from the recovered haloiminium salt raw material, and thus the haloiminium salt raw material can be recycled many times. For example, when 2-chloro-1,3-dimethylimidazolidinium chloride (hereinafter referred to simply as DMC) is used as a haloiminium salt, 1,3-dimethyl-2-imidazolidinone (hereinafter referred to simply as DMi) is formed as a byproduct. DMi is recovered by distillation, or a filtrate is obtained by filtering the isoimide suspension after finishing the reaction, and phosgene or other halogenating agent is reacted to regenerate original DMC with ease.

The isoimide compound having an isoimide bond shown by the formula (12) can be obtained by the above process. For example, the compounds represented by the formula (1), (2) or (3) and polymers or copolymers represented by the formula (4) or (5) can provide corresponding isoimide represented by the formula (1-1), (2-1), (3-1), (4-1) or (5-1), respectively.

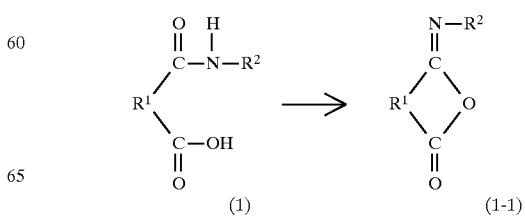

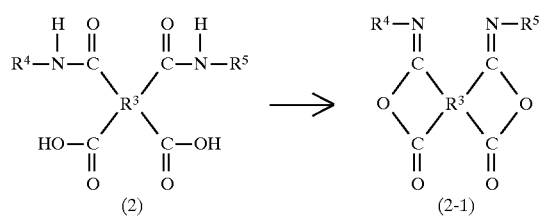
(2)     (2-1)
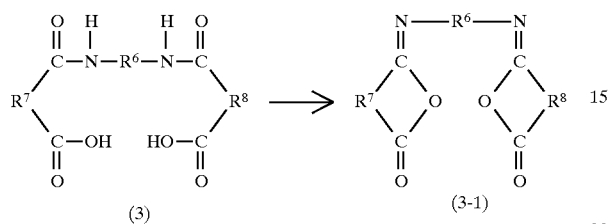
(3)     (3-1)
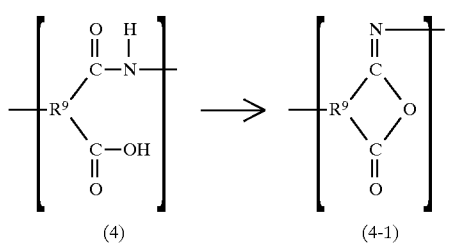
(4)     (4-1)
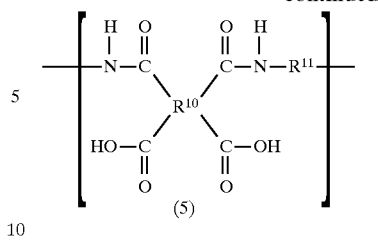
(5)
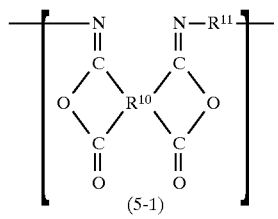
(5-1)
More specifically, for example, a diamine compound below reacts with acid anhydride to give bisamic acid and a bisisoimide compound can be obtained from bisamic acid as shown below.
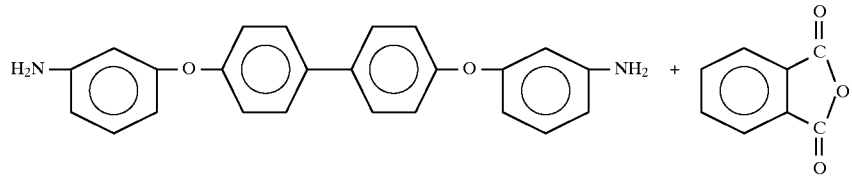
diamine compound          acid anhydride
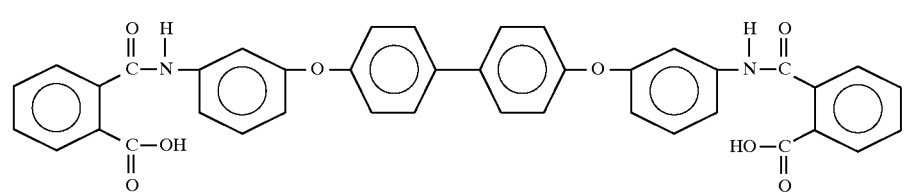
bisamic acid
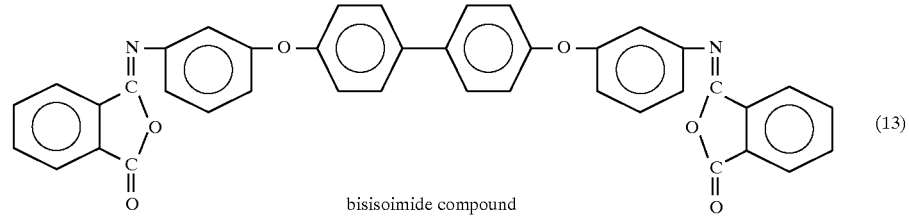
(13)
bisisoimide compound The bisisoimide compound thus obtained is a novel compound. Any of the bisisoimide compounds which are shown by the formulas (14), (15) and (16) below and can be prepared from the following diamine compounds and acid anhydride are also novel compounds.

bis(3-aminophenoxy)biphenyl+maleic anhydride
1,3-bis(3-aminophenoxy)benzene+phthalic anhydride
1,3-bis(3-aminophenoxy)benzene+maleic anhydride

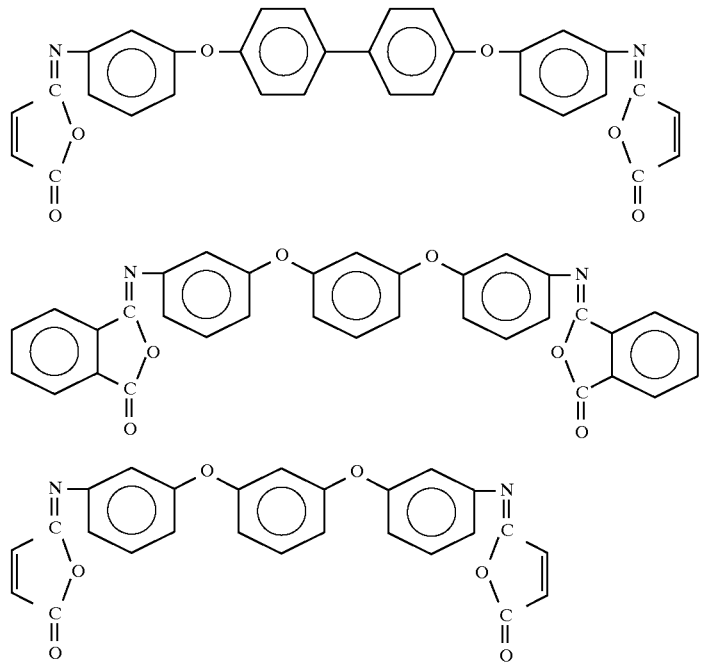

(14)

(15)

(16)

Monoisoimide obtained in the invention can be applied to a raw material of medicines, agricultural chemicals and other various matters.

Polyvalent isoimide obtained in the invention can be used as a raw material of polymers such as polyamide, polyetheramide, polyesteramide and polythioester amide in addition to medicines and agricultural chemicals.

Polyisoimide obtained in the invention can be processed into molded articles and formed items of polyisoimide and polyimide. Polyisoimide powder can be compressed into a desired form and successively sintered, or processed in a molten state. Polyisoimide solution can be applied to a glass plate, the solvent is evaporated, and residual polyisoimide is separated from the glass plate to obtain a polyisoimide film. Further, a flexible board can be prepared by coating polyisoimide solution on a copper foil and evaporating the solvent.

In addition to above, the powder, grain and solution of polyisoimide obtained in the invention can be used for the preparation of, for example, the film for a heat resistant insulation tape, heat resistant adhesive tape, high density magnetic recording base, condenser, and flexible printed circuit board (EPC); structural material reinforced with fluoro resin or carbon fiber; molded material and formed article such as bobbin of a small coil, sleeve, and terminal insulation tube; laminated material used for power transistor insulating spacer, magnetic head spacer, power relay spacer, and transformer spacer; enamel coating material used for wire and cable insulation coating, solar cell, low temperature storage tank, space craft heat insulation material, integrated circuit, and slot liner; membrane for ultrafiltration, reverse osmosis and gas separation; and heat resistant fiber used for thread, fabric and non woven fabric.

EXAMPLE

The invention will hereinafter be illustrated in detail by way of examples. However, no restriction is imposed upon the scope of the invention by these examples.

Properties of the compound in these examples were measured by the following methods.

○ Weight average molecular weight (MW)
  Equipment: shodex, GPC SYSTEM 11
  MW of polyamic acid: Eluate was a solution of lithium bromide and phosphoric acid in N,N-dimethylformamide (DMF) at a concentration of 6m M/L, respectively.
  MW of polyisoimide: Eluate was a solution of lithium bromide in N-methylpyrrolidone at a concentration of 6m M/L.
○ High performance liquid chromatography (HPLC)
  Equipment: HPLC manufactured by Nippon Bunko Co.
  Column: A-312 manufactured by YMC Co.
  Eluate: A mixture of acetonitrile and water incorporated with a proper amount of phosphoric acid and tetrabutylammonium hydroxide. The composition of eluate was suitably adjusted depending upon the compound to be measured.
○ Infrared analysis (IR)
  Equipment: IR PEPORT-100 manufactured by Nippon Bunko Co. Measured by KBr tablet method Example 1

In a flask, 29.4g (0.30 mol) of maleic anhydride, 27.9g (0.30 mol) of aniline, and 200 ml of toluene were charged, stirred at 60° C. for 4 hours, and confirmed with HPLC formation of N-phenylmaleamic acid. Thereafter, 60.86g (0.36 mol) of 2-chloro-1,3-dimethylimidazolinium chloride (DMC) and 85.32g (1.08 mol) of pyridine were added, and stirred at room temperature for an hour. The reaction mixture was immediately analysed by HPLC. Conversion rate of amic acid was 100% and selectivity of N-phenylmaleisoimide was 99.7%. The reaction mixture was filtered to remove pyridine hydrochloride, washed with water and successively with a 1% aqueous hydrogen chloride solution. Toluene was distilled off and the residue was dried under reduced pressure. As a result of IR analysis, the powder obtained had a stretching vibration of carbonyl group at 1810 cm$^{-1}$ and an absorption band of lactone ring at 900 cm$^{-1}$. Further, results of elemental analysis were C 69.42%; H 4.08%; and N 8.16%. Consequently, it was confirmed that the powder was N-phenylmaleisoimide. The powder had a melting point of 61.1° C. and the yield was 98.1%.

Examples 2 to 8

Benzene ring substituted aniline derivatives (Q—NH$_2$) and basic substances were used as shown in Table 1 and the reaction was carried out according to the conditions in Example 1. The mol ratio of maleic anhydride, aniline derivative, DMC and basic substance was the same as Example 1. Selectivity of the formed product and yield of the isolated product are shown in Table 1.

TABLE 1

| Example No. | substituted benzene ring Q | Basic substance | Selectivity % | Yield % |
| --- | --- | --- | --- | --- |
| 2 | phenyl | dimethylcyclohexyl-amine | 99.2 | 97.9 |
| 3 | phenyl | triethylamine | 99.3 | 97.2 |
| 4 | phenyl | γ-picoline | 99.0 | 93.6 |
| 5 | 3,5-dichlorophenyl | pyridine | 99.0 | 98.1 |
| 6 | 4-chlorophenyl | pyridine | 99.5 | 96.8 |
| 7 | 4-nitrophenyl | pyridine | 99.6 | 96.9 |
| 8 | 4-methylphenyl | pyridine | 99.1 | 97.1 |

Example 9

To 100 ml of acetone, 14.81g (0.10 mol) of phthalic anhydride and 18.42g (0.05 mol) of 4,4'-bis(3-aminophenoxy)biphenyl were added, and stirred at room temperature for 24 hours to obtain a suspension of bisamic acid. To the suspension, 18.60g (0.11 mol) of DMC and 26.07g (0.33 mol) of pyridine were added and stirred at room temperature for an hour. After addition of DMC and pyridine, the suspension varied to orange. At the time after reacting for an hour, the suspension was analyzed by HPLC. Bisamic acid was completely disappeared and conversion rate was 100%. Selectivity of bisisoimide was 99.5%. The suspension was mixed with 100 ml of water and filtered. The filter cake was washed with a 1% aqueous hydrochloric acid solution and water and dried to obtain 30.61g of bisisoimide. The yield of isolated product was 97.4%. The product was recrystallized by using methylene chloride and ether and dried. The recrystallized bisisoimide powder had purity of 99.5% by HPLC analysis. IR analysis observed absorption bands originated from isoimide at 1820 cm$^{-1}$ and 920 cm$^{-1}$. Results of elemental analysis were C 76.48%; H 3.94%; and N 4.45%. C$^{13}$NMR analysis was also carried out.

Results of these anaylysis confirmed that the bisisoimide powder was 4,4-bis(3-phthalimidophenoxy)biphenyl. The bisisoimide powder had a melting point of 207.8 to 209.9° C. As a result of differential scanning colorimetry (DSC) in the temperature range of 40 to 400° C., a melt absorption peak was observed at 204.1° C. and an exothermic peak derived from imide conversion was observed at 302.0° C.

Figure 2:
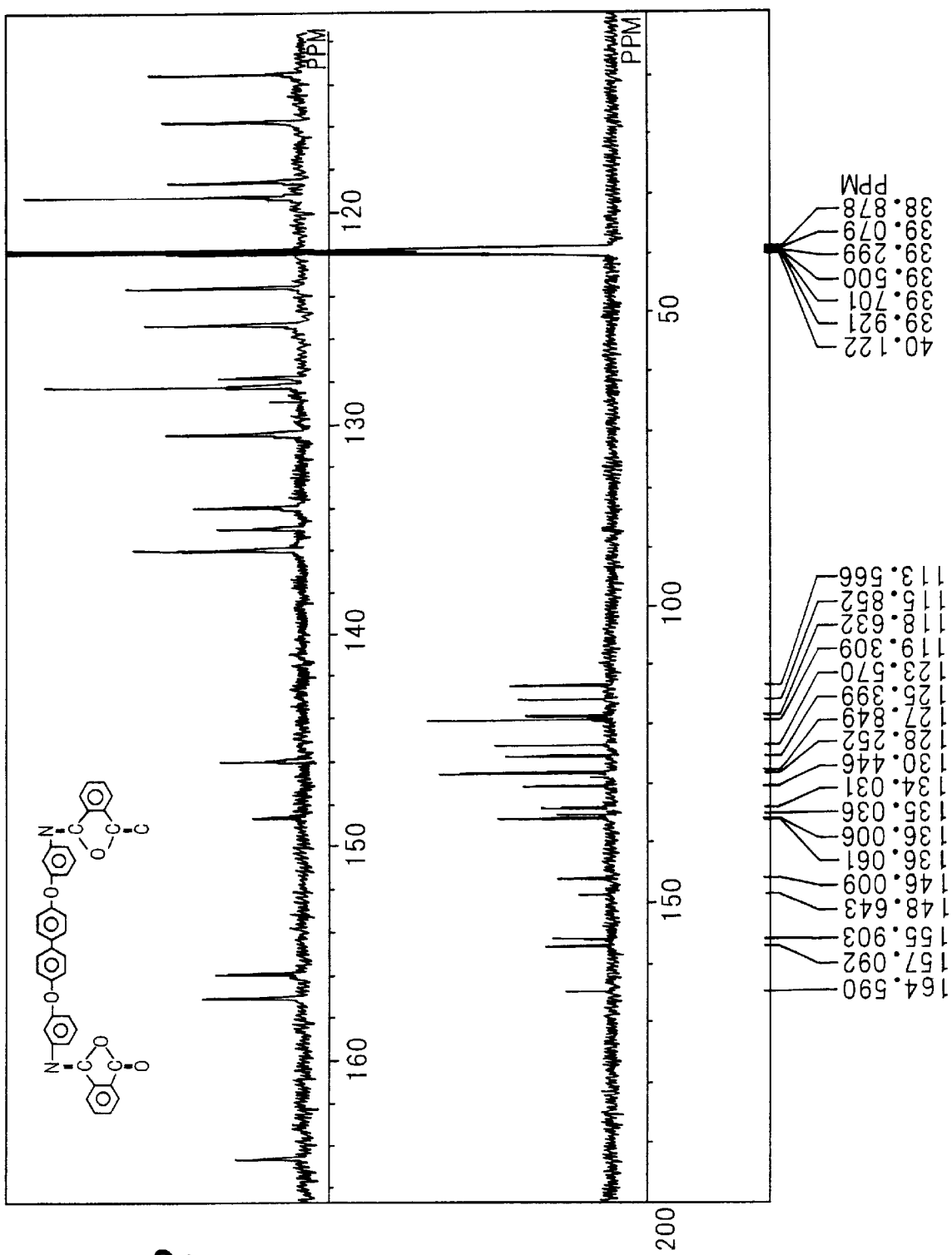
FIG. 2 shows a $C^{13}$NMR chart of 4,4'-bis(3-phthalisoimidophenoxy) biphenyl obtained in Example 9.
Figure 3:
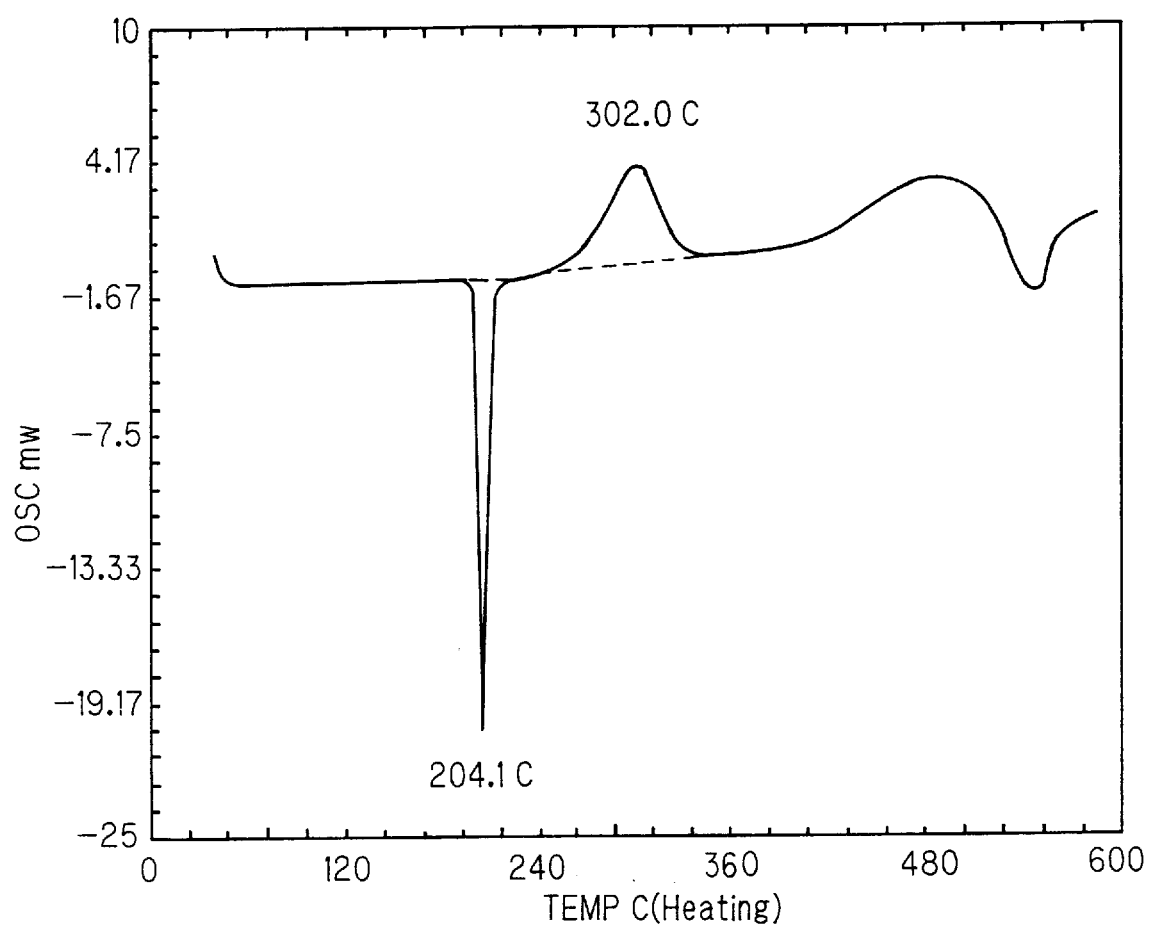
FIG. 3 shows a DSC chart obtained in Example 9.

An IR chart, C$^{13}$NMR chart and DSC chart of 4,4'-bis(3-phthalisoimidophenoxy)biphenyl obtained are individually illustrated in FIG. 1, FIG. 2 and FIG. 3. Further, bisisoimide thus obtained was heated at 350° C. for 15 minutes and cooled. Thus treated bisisoimide had a melting point of 288.9 to 294.3° C. In the IR spectrum, the absorption bands of isoimide at 1820 cm$^{-1}$ and 920 cm$^{-1}$ were completely disappeared and absorption bands derived from imide was observed at 1780 cm$^{-1}$ and 615 cm$^{-1}$ as a substitute. Thus, conversion to 4,4'-bis(3-phthalimidophenoxy)biphenyl was confirmed.

Examples 10 to 15

Diamines were used as shown in Table 2 and the reaction was carried out according to the conditions in Example 9. The mol ratio of phthalic anhydride, diamine, DMC and pyridine was the same as Example 9. The reaction mixture was incorporated with 100 ml of water and filtered. The filter cake was washed with a 1% aqueous hydrochloric acid solution and water, and dried to obtain the desired product. Selectivity of the reaction and yield of the isolated product are illustrated in Table 2.

TABLE 2

| Example No. | Diamine | Seletivity % | Yield % |
| --- | --- | --- | --- |
| 10 | m-phenylenediamine | 99.1 | 96.8 |
| 11 | p-phenylenediamine | 99.5 | 98.2 |
| 12 | 4,4'-diaminodiphenyl-ether | 99.0 | 97.1 |
| 13 | 1,3-bis(4-aminophenoxy)-benzene | 99.3 | 92.9 |
| 14 | bis(4-aminophenyl)methane | 99.1 | 94.6 |
| 15 | hexamethylenediamine | 98.9 | 91.4 |

Example 16

To reactor, 36.84g (0.1 mol) of 4,4-bis(3-aminophenoxy) biphenyl, 20.50g (0.094 mol) of pyromellitic dianhydride, 1.77g (0.012 mol) of phthalic anhydride, and 250g of 1-methyl-2-pyrrolidone were charged and reacted with stirring at 60° C. for 4 hours to obtain a polyamic acid solution. Polyamic acid had MW of 76,000. To the solution, 37.19g (0.22 mol) of DMC and 46.93g (0.594 mol) of pyridine were added and stirred at room temperature for 2 hours. The reaction mixture was diluted with 300 ml of acetone, filtered, washed, and dried to obtain polymer powder having MW of 63,000. IR analysis observed isoimide originated absorption bands at 1820 cm$^{-1}$ and 920 cm$^{-1}$ and thus as confirmed.

Example 17

To a reactor, 13.31g (0.10 mol as COOH group) of polyamic acid which was prepared from aspartic acid, 20.75g (0.12 mol) of DMC, and 50g of 1,3-dimethyl-2-imidazolidinone (DMi) were charged. To the resulting solution, 28.44g (0.36 mol) of pyridine was dropwise added over 30 minutes and successively stirred at room temperature for 2 hours. The reaction mixture was poured into a large amount of acetone. The precipitate was filtered, washed and dried to obtain polymer powder. The polymer had MW of 138,000 and exhibited absorption bands at 1820 cm$^{-1}$ and 920 cm$^{-1}$ in IR analysis. Thus polysuccinic acid isoimide was identified.

Example 18

To a reactor, 18.42g (0.05 mol) of 4,4'-bis(3-aminophenoxy) biphenyl, 10.36g (0.0475 mol) of pyromellitic dianhydride, 0.74g (0.005 mol) of phthalic anhydride, and 115g of DMi were charged and reacted in a nitrogen atmosphere at 60° C. for 4 hours to obtain a polyamic acid solution. To the solution, 21.98g (0.13 mol) of DMC and 26.07g (0.33 mol) of pyridine were added and stirred at room temperature for 3 hours. After finishing the reaction, the reaction mixture is poured into a large amount of toluene. The precipitate was filtered, washed and dried to obtain 26.28g of polymer powder. Yield was 94.8%. The polymer obtained had MW of 82,000 and IR analysis exhibited absorption bands at 1820 cm$^{-1}$ and 920 cm$^{-1}$. Thus, polyisoimide was identified.

Example 19

To a reactor, 10.01g (0.1 mol) of 4,4'-diaminodiphenyl ether, 20.50g (0.094 mol) of pyromellitic dianhydride, 1.77g (0.012 mol) of phthalic anhydride, and 250g of 1-methyl-2-pyrrolidone were charged and reacted with stirring at 60° C. for 4 hours to obtain a polyamic acid solution. To the solution, 37.19g (0.22 mol) of DMC and 46.93g (0.594 mol) of pyridine were added and stirred at room temperature for 2 hours. The reaction mixture was poured into a large amount of toluene. The precipitate was filtered, washed and dried to obtain polymer. The polymer thus obtained had MW of 71,000 and IR analysis exhibited absorption bands at 1820 cm$^{-1}$ and 920 cm$^{-1}$. Thus, polyisoimide was identified.

Example 20

To a 1000 ml separable flask, 12.514g (57.37m mol) of pyromellitic dianhydride (PMDA) and 140g of tetrahydrofuran (THF) were charged and stirred sufficiently at room temperature to obtain a solution. To the solution, a solution containing 11.49g (57.37m mol) of 4,4'-diaminodiphenyl ether (ODA) in 240g of THF was dropwise added with stirring over an hour. After finishing addition of the diamine solution, the reaction mixture was stirred at room temperature for 24 hours to obtain a polyamic acid suspension. Polyamic acid had MW of 322,000.

To the suspension obtained, 21.34g (126.2m mol) of DMC was added and stirred at 10° C. or less and further 29.9g (378.6m mol) of pyridine was dropwise added over 30 minutes. The suspension turned orange simultaneously with addition of pyridine. After addition of pyridine, the reaction mixture was returned to the room temperature, stirred for 2 hours. The polyisoimide suspension thus obtained was filtered. The filter cake was washed with water and acetone and dried at 40° C. for 12 hours under reduced pressure to obtain granular polyisoimide. The IR spectrum of the granule lost the amic acid originated absorption band at 1540 cm$^{-1}$ and exhibited an isoimide originated peak at 920 cm$^{-1}$ as a substitute. Further, the absorption band originated from imide which was usually observed at 610 cm$^{-1}$ could not be found at all.

The polyisoimide granule was heat treated at 80° C. for 5 hours and successively at 300° C. for 5 hours to obtain polyimide granule. The IR spectrum lost the isoimide originated absorption band at 920 cm$^{-1}$ and exhibited an imide originated absorption band at 610 cm$^{-1}$ as a substitute. Polyimide granule thus obtained had no Tg at temperature lower than 350° C. as a result of a differential scanning calorimeter measurement and thus was excellent in heat resistance.

Example 21

To a 200 ml three necked flask, 2.181g (10m mol) of PMDA and 40g of THF were charged and sufficiently stirred at room temperature to obtain a solution. To the solution, 1.242g (5m mol) of diaminodiphenyl sulfone (DDS) was added in the form of granule as intact. The reaction mixture immediately turned deep-red transparent liquid and became turbid after stirring for 30 minutes. After 3 hours from addition of DDS, a light yellow suspension was obtained. To the suspension, a solution containing 1.001g (5m mol) of ODA in 40g of THF was added over 2 hours and stirred at room temperature for 24 hours after finishing the addition. A white polyamic acid suspension was obtained. Polyamic acid had MW 150,000.

To the suspension obtained, 3.72g (22m mol) of DMC was added and stirred at 10° C. or less temperature, and successively 5.33g (57.2m mol) of β-picoline was gradually added. After finishing addition of β-picoline, the mixture was returned to room temperature and stirred for 2 hours to obtain a polyisoimide suspension. The suspension was filtered, washed with water and THF and dried at 40° C. for 5 hours under reduced pressure to obtain polyisoimide granule.

The granule had MW of 127,000. The IR spectrum of the granule lost the absorption band originated from amic acid at 1540 cm$^{-1}$ and exhibited an absorption band originated from isoimide at 920 cm$^{-1}$ was confirmed as a substitute. Further, the absorption band originated from imide could not be found. Polyimide granule was obtained by heat treating the polyisoimide granule at 80° C. for 5 hours and successively at 300° C. for 5 hours. The IR spectrum of the heat-treated granule lost the absorption band originated from isoimide at 920 cm$^{-1}$ and an absorption band originated from imide at 610 cm$^{-1}$ was found as a substitute.

Example 22

The polyisoimide granule obtained in Example 21 was dissolved in N-methylpyrrolidone (NMP) to obtain a 15 wt % polyisoimide solution. The solution was coated on a glass plate with a film applicator so as to obtain a thickness of 200 μm. Drying and imidization was successively carried out at 60° C. for 2 hours, 80° C. for 5 hours, and 300° C. for 5 hours in an inert oven. After cooling gradually, the glass plate was immersed in water to separate a polyimide film from the glass plate. Tg of the polyimide film was not observed at 350° C. or less by DSC measurement. The film had heat decomposition temperature of 587° C. as a result of TGA measurement and thus heat resistance of the film was excellent.

Example 23

To a 200 ml three necked flask, 2.181g (10.00m mol) of PMDA and 40g of THF were charged and sufficiently stirred at room temperature to obtain a PMDA solution. Separately, a solution was prepared by dissolving 1.242g (5m mol) of DDS and 1.001g (5m mol) of ODA in a solvent mixture of 32g of THF and 8g of acetone. The solution thus obtained was added to the above PMDA solution over 2 hours. After finishing addition, stirring was continued at room temperature for 24 hours to obtain a white polyamic acid suspension. Polyamic acid had MW of 123,000. To the suspension obtained, 3.72g (22m mol) of DMC was added and stirred at 10° C. or less temperature. To the mixture obtained, 6.15g (66m mol) of β-picoline was dropwise added over 15 minutes. After finishing β-picoline addition, the reaction mixture was returned to room temperature and stirred for 2 hours to obtain a polyisoimide suspension. The suspension was filtered, washed with water and THF and dried at 40° C. for 6 hours to obtain polyisoimide granule.

The granule had MW of 117,000. The IR spectrum of the granule lost the absorption band originated from amic acid at 1530 cm$^{-1}$ and exhibited an absorption band originated from isoimide at 920 cm$^{-1}$ as a substitute. The polyimide granule was heat treated at 80° C. for 5 hours and at 300° C. for 5 hours to obtain polyimide granule. The IR spectrum of polyimide granule thus obtained lost the absorption spectrum originated from isoimide at 920 cm$^{-1}$ and exhibited an absorption band originated from imide at 605 cm$^{-1}$ as a substitute. Tg of the polyimide granule was not observed at 350° C. or less. The granule had a heat decomposition initiation temperature of 594° C. as a result of TGA measurement and thus heat resistance of the granule was excellent.

Example 24

The polyisoimide granule obtained in Example 23 was dissolved in NMP to obtain a 15 wt % polyisoimide solution. The solution was coated on a glass plate with a film applicator so as to obtain a thickness of 200 μm, and drying and imidization were carried out by heating at 60° C. for 2 hours and 80° C. for 4 hours in an inert oven. The glass plate was gradually cooled and immersed in water to separate a polyimide film from the glass plate. Tg of the polyimide film was not observed at 350° C. or less temperature as a result of DSC measurement. The film had a heat decomposition initiation temperature of 594° C. as a result of TGA measurement and thus the heat resistance of the film was excellent.

Example 25

To a 200 ml three necked flask, 2.181g (10.00m mol) of PMDA and 40g of THF were charged, and sufficiently stirred at room temperature to obtain a PMDA solution. To the solution obtained, 0.745g (3m mol) of DDS was added in the form of powder as intact. After 3 hours from addition of DDS, the reaction mixture turned to a light yellow suspension. To the suspension, a solution containing 1.401g (7m mol) of ODA in 40g of THF was added over 2 hours and thereafter stirred at room temperature for 24 hours to obtain a light yellow polyamic acid suspension. Polyamic acid had MW of 183,000. To the suspension obtained, 3.72g (22m mol) of DMC was added and stirred at 10° C. or less temperature and 5.22g (66m mol) of pyridine was dropwise added over 15 minutes. After addition of pyridine, the mixture was returned to room temperature and stirred for 3 hours to obtain a light yellow polyamic acid suspension. The suspension was filtered, washed with water and THF, and dried at 40° C. for 6 hours to obtain polyisoimide granule.

The granule had MW of 163,000. The IR spectrum of the granule lost the absorption band originated from amic acid at 1530 cm$^{-1}$ and exhibited an absorption band originated from isoimide at 920 cm$^{-1}$ as a substitute. The polyimide granule was heat treated at 80° C. for 5 hours and at 300° C. for 5 hours to obtain polyimide granule. The IR spectrum of polyimide granule lost the absorption band originated from isoimide at 920 cm$^{-1}$ and exhibited an absorption band originated from imide at 605 cm$^{-1}$ as a substitute. Tg of the polyimide granule was not observed at 350° C. or less temperature and thus heat resistance was excellent.

Example 26

To 150g of DMF, 39.22g (0.4 mol) of maleic anhydride and 73.69g (0.2 mol) of 4,4'-bis(3-aminophenoxy)biphenyl were added, and stirred at 60° C. for 6 hours. Thereafter, 150g of water were mixed, filtered and washed with water and further isopropylalcohol, and dried to obtain bisamic acid.

To flask, 56.46g (0.1 mol) of the bisamic acid, 37.19 (0.22 mol) of DMC and 250g of benzene were charged. 55.88g (0.6 mol) of β-picoline was dropwise added over 15 minutes while cooling with ice water.

Thereafter, the mixture was returned to room temperature and successively stirred for an hours to obtain a polyisoimide suspension. The suspension was charged to 1 liter of IPA, and stirred and filtered, the filter cake was sludged in 200 ml of IPA and filtered, the sludging and filtering were repeated 3 times and the resulting cake was dried for 8 hours under pressure of 40 mm Hg at temperature of 50° C. to obtain 50.4g of white brown powder. Yield was 95.4%.

Further, by repeatedly recrystallizing the powder in methylene chloride/IPA (weight ratio 2/1) solution and drying to obtain pale yellow powder.

Result of elemental analysis of the bismaleisoimide powder thus obtained was C 72.70%, H 3.84%, N 5.27% and was the same as calculation(C 72.72%, H 3.81%, N 5.30%). From the result of IR analysis, absorption band of C=O stretching vibration at 1790 cm$^{-1}$ and absorption band of C=N stretching vibration at 1670 cm$^{-1}$ were confirmed.

From these results, the powder obtained was confirmed to be 4,4'-bis(3-maleisoimidophenoxy)biphenyl.

Figure 4:
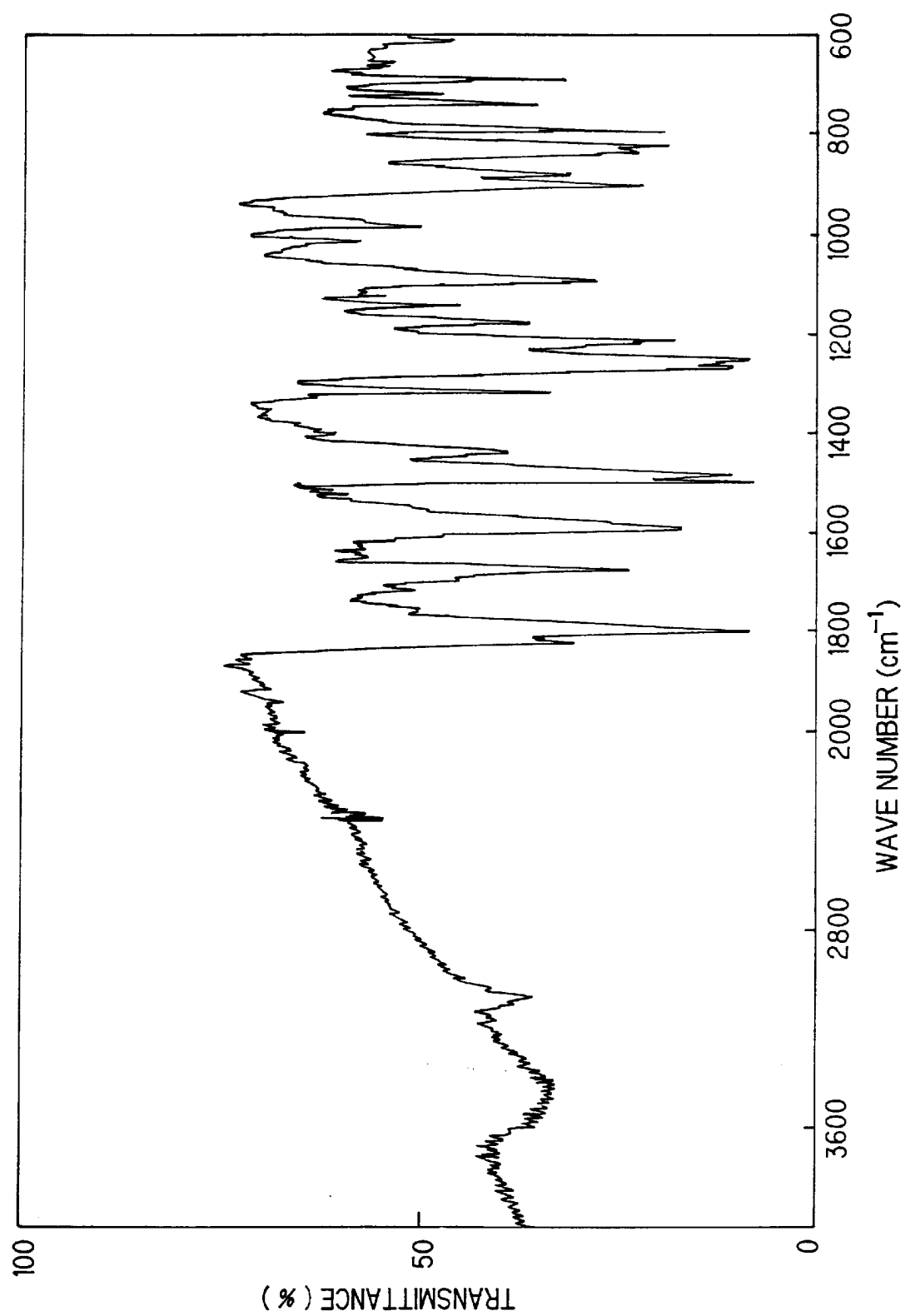
FIG. 4 shows an IR chart of 4,4'-bis(3-maleisoimidophenoxy) biphenyl obtained in Example 26.

Melting point was 173.1 to 175.2° C. IR chart of 4,4'-bis(3-maleisoimidophenoxy)biphenyl was shown in FIG. 4.

Example 27

The same procedure as Example 26 was carried out except that 4,4'-bis(3-aminophenoxy)biphenyl was used in place of 4,4'-bis(3-aminophenoxy)benzene and in accordance with Example 26 about all of mole ratio for raw materials, amount of solvent and others.

The result of elemental analysis of the resulting white powder was C 69.02%, H 3.60%, N 6.17% and was the same as calculation(C 69.03%, H 3.56%, N 6.19%).

From the result of IR analysis, absorption band of C=O stretching vibration at 1790 cm$^{-1}$ and absorption band of C=N stretching vibration at 1670 cm$^{-1}$ were confirmed.

From these results, the powder obtained was confirmed to be 4,4'-bis(3-maleisoimidophenoxy)benzene.

Figure 5:
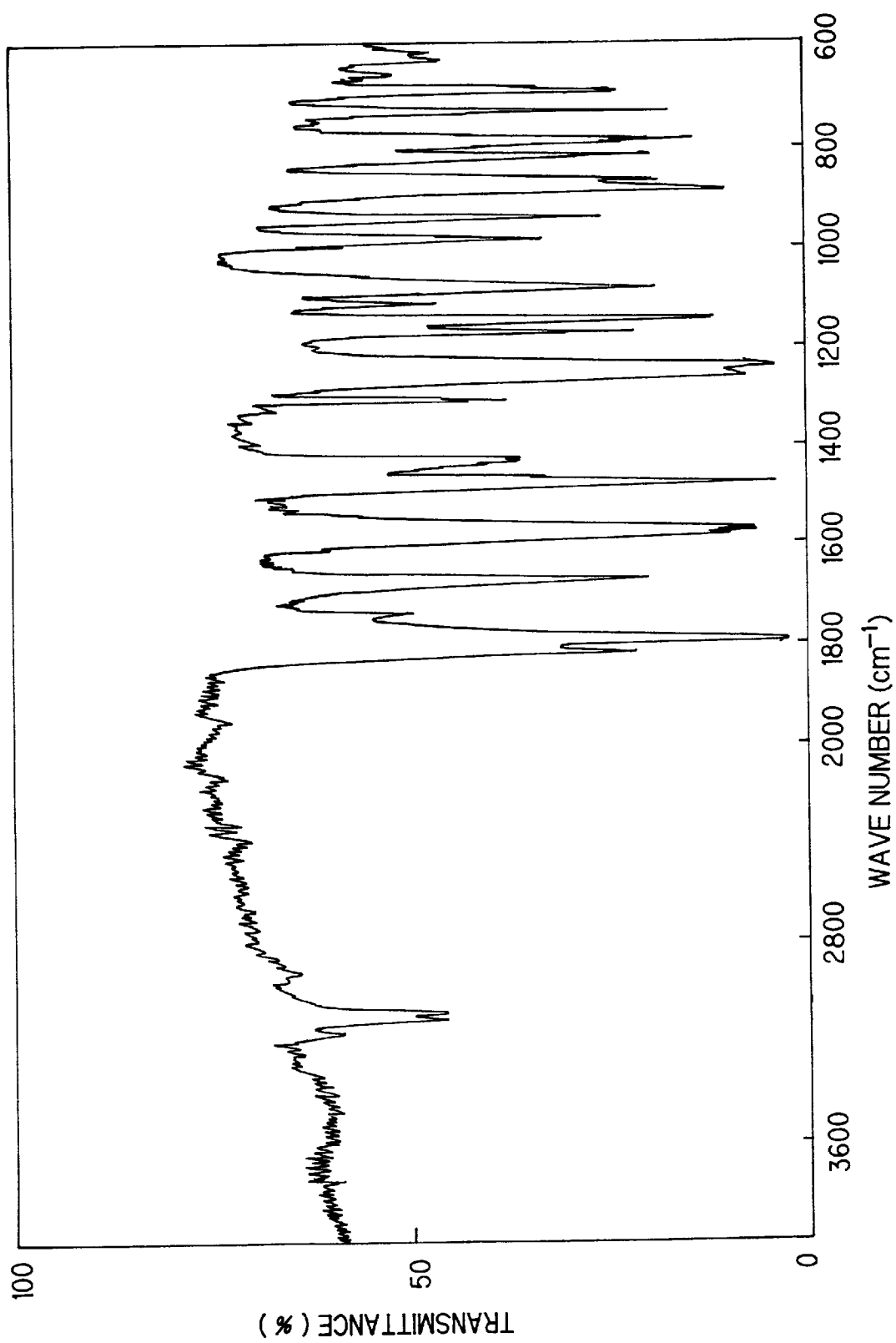
FIG. 5 shows an IR chart of 4,4'-bis(3-maleisoimidophenoxy)benzene obtained in Example 27.

Melting point was 156.8 to 158.5° C. IR chart of 4,4'-bis(3-maleisoimidophenoxy)benzene was shown in FIG. 5.

Comparative Example 1

After preparing a bisamic acid solution by the same process as Example 9, 31.50g (0.15 mol) of trifluoroacetic anhydride and 20.24g (0.20 mol) of triethylamine were added and stirred at room temperature. After an hour from initiation of the reaction, HPLC measurement was carried out, conversion rate was 89.1% and selectivity was 87.1%. Thus, reaction velocity was slow and selectivity was low as compared with Example 9. The reaction required 3 hours in order to obtain a conversion rate of 99% or more.

Comparative Example 2

After preparing a bisamic acid solution by the same method as Example 9, 24.76g (0.12 mol) of dicyclohexylcarbodiimide was added and stirred at room temperature. After an hour from initiation of the reaction, HPLC measurement was carried out, conversion rate was 94.8% and selectivity was 34.6%. Thus, both conversion rate selectivity were low as compared with Example 9.

In the reaction, a large amount of bisimide and imide-isoimide was formed in addition to bisisoimide.

Comparative Example 3

A polyamic acid suspension was prepared by the same method as Example 20. To the suspension, 11.61g (114.74m mol) of triethylamine was added and stirred at 0° C. and successively 24.10g (114.74m mol) of trifluoroacetic anhydride (TFAA) was added over 2 hours. After addition of TFAA, the reaction mixture was returned to room temperature and stirring was continued for 2 hours to obtain a polyisoimide suspension. The suspension was filtered and dried at 40° C. for 3 hours under reduced pressure to obtain polyisoimide granule. The IR spectrum of the granule exhibited an absorption band originated from amic acid 1540 cm$^{-1}$. Thus, isoimidization was found insufficient within the reaction time of 2 hours.

Comparative Example 4

A polyamic acid suspension was prepared by the same process as Example 21. To the polyamic acid suspension, 2.02g (20.0m mol) of triethylamine was added and stirred at 0° C. and successively 4.28g (20.4m mol) of TFAA was gradually added. After addition of TFAA, the reaction mixture was returned to room temperature and stirred for 2 hours to obtain a polyisoimide suspension. The suspension was filtered and the granule obtained was dried at 40° C. for 3 hours under reduced pressure to obtain polyisoimide granule.

IR spectrum of the granule exhibited an absorption band originated from amic acid at 1530 cm$^{-1}$ and also an absorption band originated from imide. Thus the reaction time of 2 hours was insufficient for isoimidization and selectivity was also poor. The polyisoimide granule thus obtained was dissolved in NMP to prepare a 15 wt % polyisoimide solution. The solution was coated on a glass plate with a film applicator so as to obtain a thickness of 20 μm. Drying and imidization was carried out by heating successively at 60° C. for 2 hours, at 80° C. for 5 hours and at 300° C. for 5 hours in an inert oven.

After cooling gradually, the glass plate was immersed in water and a polyimide film was separated from the glass plate. The polyimide film comprised many bubbles. It was considered that an amic acid bond was remained in polyisoimide obtained, a water molecule generated by dehydrating condensation reaction in the imidization step, and the generated water led to bubble development.

What is claimed is:

1. A preparation process of isoimide comprising reacting a compound having one or more carboxyl group and one or more amide bond in the same molecule in the presence of a haloiminium salt and basic substance.

2. A preparation process of isoimide comprising reacting a compound having one or more carboxyl group with a compound having one or more amide bond in the presence of a haloiminium salt and basic substance.

3. A preparation process according to claim 1 wherein the compound having one or more carboxyl group and one or more amide bond in the same molecule is represented by one of the formula (1), (2) and (3) or mixture of the same,

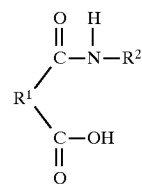

(1)

wherein $R^1$ is an unsubstituted or substituted divalent hydrocarbon group, individually selected from an aliphatic group and aromatic group, have a saturated bond and/or unsaturated bond, and $R^2$ is an unsubstituted or substituted monovalent hydrocarbon group, individually selected from an aliphatic group and aromatic group, have a saturated bond and/or unsaturated bond,

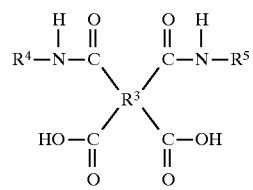

(2)

wherein $R^3$ is an unsubstituted or substituted tetravalent hydrocarbon group, is an aliphatic group or aromatic group, and has a saturated bond and/or unsaturated bond; or $R^4$ and $R^5$ are an unsubstituted or substituted monovalent hydrocarbon group, individually selected from an aliphatic group and aromatic group, have a saturated bond and/or unsaturated bond, and are the same or different,

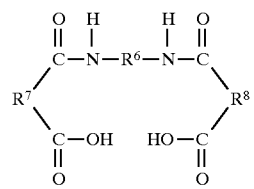

(3)

wherein $R^6$ is an unsubstituted or substituted divalent hydrocarbon group, is an aliphatic group or aromatic group, and has a saturated bond and/or unsaturated bond; and $R^7$ and $R^8$ are an unsaturated or saturated divalent hydrocarbon group and are the same or different.

4. A preparation process according to claim 1 wherein the compound having one or more carboxyl group and one or more amide bond in the same molecule is a homopolymer or copolymer having recurring units represented by the formula (4) and/or formula (5),

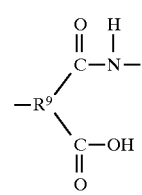

(4)

wherein $R^9$ is an unsubstituted or substituted trivalent hydrocarbon group, is an aliphatic group or aromatic group, and has a saturated bond and/or unsaturated bond,

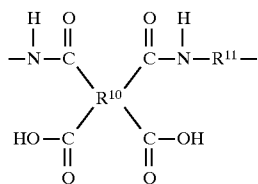 (5)

wherein $R^{10}$ is an unsubstituted or substituted tetravalent hydrocarbon group, is an aliphatic group or aromatic group, and has a saturated bond and/or unsubstituted bond.

5. A preparation process according to claim 1 wherein the compound having one or more carboxyl group and one or more amide bond in the same molecule is obtained by reacting a compound having one or more acid anhydride group.

6. A preparation process according to claim 1 wherein the compound having one or more carboxyl group and one or more amide bond in the same molecule is obtained by reacting a compound having one or more amino group with a compound having one or more acid halogenide group and one or more carboxyl group in the same molecule.

7. A preparation process according to claim 1 wherein the compound having one or more carboxyl group and one or more amide bond in the same molecule is obtained by reacting a compound having one or more amino group with a compound having two or more acid halogenide group in the same molecule and successively converting the unreacted acid halogenide group in the connected molecule to a carbonyl group.

8. A preparation process according to claim 1 wherein the compound having one or more carboxyl group and one or more amide bond in the same molecule is obtained by reacting a compound having one or more amino group with a compound having two or more carboxyl group.

9. A preparation process according to claim 1 wherein the compound having one or more carboxyl group and one or more amide bond in the same molecule is obtained by reacting a compound having one or more amide group and/or amide bond with a compound having one or more carboxyl group.

10. A preparation process according to claim 1 wherein the compound having one or more carboxyl group and one or more amide bond in the same molecule is a polymer of amino acid.

11. A preparation process according to claim 2 wherein the compound having one or more amide bond is a compound represented by the formula (6), (7) or (8) below or a mixture of the same,

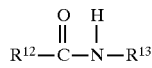 (6)

wherein $R^{12}$ and $R^{13}$ are an unsubstituted or substituted monovalent hydrocarbon group, individually selected from an aliphatic group or aromatic group, have a saturated bond and/or unsaturated bond, and are the same or different,

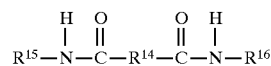 (7)

wherein $R^{14}$ is an unsubstituted or substituted divalent hydrocarbon group, is an aliphatic group or aromatic group, and has a saturated bond and/or unsaturated bond; and $R^{15}$ and $R^{16}$ are an unsubstituted or substituted monovalent hydrocarbon group, individually selected from an aliphatic group and aromatic group, have a saturated bond and/or unsaturated bond, and are the same or different,

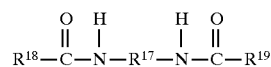 (8)

wherein $R^{17}$ is an unsubstituted or substituted divalent hydrocarbon group, is an aliphatic group or aromatic group and has a saturated bond and/or unsaturated bond; and $R^{18}$ and $R^{19}$ are an unsubstituted or substituted monovalent hydrocarbon group, individually selected from an aliphatic and aromatic group, have a saturated bond and/or unsaturated bond, and the same or different.

12. A preparation process according to claim 2 wherein the compound having one or more amide bond is a polymer or copolymer having recurring units represented by the formula (9) or (10) below,

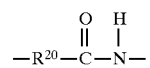 (9)

wherein $R^{20}$ is an unsubstituted or substituted divalent hydrocarbon group, is an aliphatic group or aromatic group, and has a saturated bond and/or unsaturated bond,

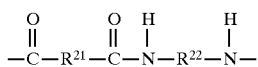 (10)

wherein $R^{21}$ and $R^{22}$ are an unsubstituted or substituted divalent hydrocarbon group, individually selected from an aliphatic group and aromatic group, have a saturated bond or unsaturated bond, and are the same or different.

13. A preparation process according to claim 2 wherein the compound having one or more amide bond is obtained by reacting a compound having one or more amino group with acid anhydride.

14. A preparation process according to claim 2 wherein the compound having one or more amide bond is obtained by reacting a compound having one or more amino group with a compound having one or more acid halogenide group.

15. A preparation process according to claim 2 wherein the compound having one or more amide group is obtained by reacting a compound having one or more amino group with a compound having one or more carboxyl group.

16. A preparation process according to claim 1 wherein the reaction is carried out at temperature from −10° C. to 150° C.

17. A bisisoimide compound having the formula (13),

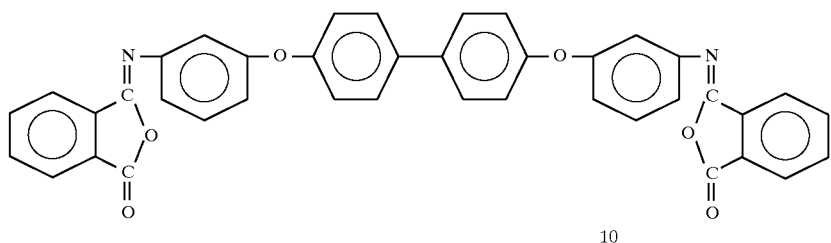
(13)
18. A bisisoimide compound having the formula (14),
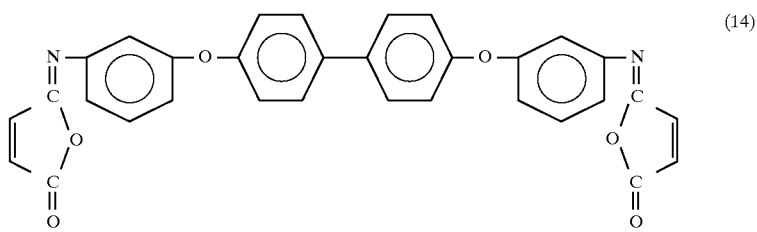
(14)
19. A bisisoimide compound having the formula (15),
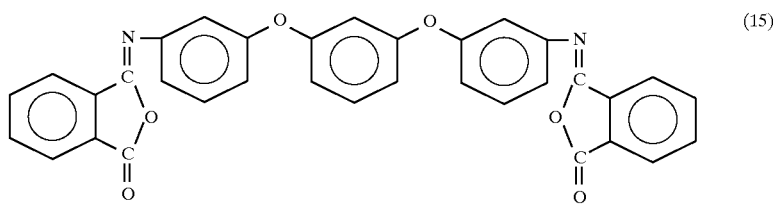
(15)
20. A bisisoimide compound having the formula (16),
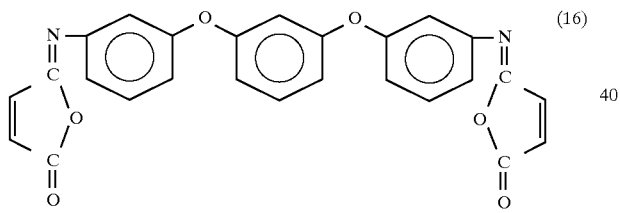
(16)
21. A preparation process according to claim 1 wherein the reaction is carried out at temperature from −10° C. to 150° C.
* * * * *

UNITED STATES PATENT AND TRADEMARK OFFICE
CERTIFICATE OF CORRECTION

PATENT NO. : 5,892,061
DATED : April 6, 1999
INVENTOR(S) : Kan Ikeda, et. al.

It is certified that error appears in the above-identified patent and that said Letters Patent is hereby corrected as shown below:

Title page, item [30] under Foreign Application Data add -- December 6, 1996 [JP]  Japan.......... 8-326595 --.

Signed and Sealed this

Fourth Day of July, 2000

Attest:

Q. TODD DICKINSON

*Attesting Officer*  *Director of Patents and Trademarks*